(12) United States Patent
Accisano, III et al.

(10) Patent No.: US 7,736,331 B2
(45) Date of Patent: Jun. 15, 2010

(54) DRAINAGE CATHETER HUB WITH WELDED SUTURE AND SIDEWALL STYLET

(75) Inventors: Nicholas Gerald Accisano, III, Howell, NJ (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 1072 days.

(21) Appl. No.: 11/078,939

(22) Filed: Mar. 11, 2005

(65) Prior Publication Data

US 2006/0206096 A1 Sep. 14, 2006

(51) Int. Cl.
*A61M 31/00* (2006.01)
*A61M 37/00* (2006.01)
A61M 29/00 (2006.01)
A61M 1/00 (2006.01)

(52) U.S. Cl. .................. 604/95.04; 604/104; 604/540

(58) Field of Classification Search ............... 604/95.04, 604/104, 95.01, 106, 107, 164.02, 165.04, 604/97.02, 523, 180, 170.01, 264, 35, 43, 604/533, 266, 528; 606/232, 108, 144, 130, 606/172, 139, 153
See application file for complete search history.

(56) References Cited

U.S. PATENT DOCUMENTS

| | | |
|---|---|---|
| 1,207,479 A | 12/1916 | Bisgaard |
| 3,315,592 A | 4/1967 | Lems |
| 3,513,848 A | 5/1970 | Winston et al. |
| 3,798,687 A | 3/1974 | Stevens |
| 3,924,633 A | 12/1975 | Cook et al. |
| 4,206,910 A | 6/1980 | Biesemeyer |
| 4,573,981 A | 3/1986 | McFarlane |
| 4,586,923 A | 5/1986 | Gould et al. |
| 4,643,720 A | 2/1987 | Lanciano |
| 4,738,667 A | 4/1988 | Galloway |

(Continued)

FOREIGN PATENT DOCUMENTS

WO  WO 2006/098818  9/2006

(Continued)

OTHER PUBLICATIONS

Angiodynamics, Abscession Drainage Catheter: A Quick Guide to the Locking Mechanism, AngioDynamics, Inc., Nov. 1999.

(Continued)

*Primary Examiner*—Nicholas D Lucchesi
*Assistant Examiner*—Ian K Holloway
(74) *Attorney, Agent, or Firm*—Stoel Rives LLP

(57) ABSTRACT

A drainage catheter having a weld to secure the distal end of the catheter in an anchor configuration. The suture is welded into a loop at the distal end of the suture to secure the anchor configuration of the distal end of the catheter either directly or by securing the suture to a stylet positioned in the catheter wall. A plurality of drainage bores are positioned on the inside diameter of the anchor loop to provide advantageous draining of fluid into the lumen of the catheter. The drainage catheter includes a stylet and stylet lumen positioned in the sidewall of the catheter approximately 90 degrees from the inside diameter of the catheter tube and drainage allowing the drainage bores on the inside diameter of the drainage catheter to operate without obstruction from the stylet and suture.

30 Claims, 9 Drawing Sheets

U.S. PATENT DOCUMENTS

| | | | |
|---|---|---|---|
| 4,740,195 A | 4/1988 | Lanciano | |
| 4,787,892 A | 11/1988 | Rosenberg | |
| 4,885,503 A | 12/1989 | Takahashi et al. | |
| 5,052,998 A | 10/1991 | Zimmon | |
| 5,074,484 A | 12/1991 | Kray | |
| 5,078,684 A | 1/1992 | Yasuda | |
| 5,213,575 A | 5/1993 | Scotti | |
| 5,308,318 A * | 5/1994 | Plassche, Jr. | 604/540 |
| 5,352,198 A | 10/1994 | Goldenberg et al. | |
| 5,399,165 A | 3/1995 | Paul, Jr. | |
| 5,419,764 A | 5/1995 | Roll | |
| 5,472,435 A | 12/1995 | Sutton | |
| 5,489,269 A | 2/1996 | Aldrich et al. | |
| 5,522,400 A | 6/1996 | Williams | |
| 5,549,331 A | 8/1996 | Yun et al. | |
| 5,666,970 A | 9/1997 | Smith | |
| 5,693,083 A | 12/1997 | Baker et al. | |
| 5,704,926 A | 1/1998 | Sutton | |
| 5,730,724 A | 3/1998 | Plishka et al. | |
| 5,806,202 A | 9/1998 | Blackman et al. | |
| 5,893,880 A | 4/1999 | Egan et al. | |
| 5,904,648 A | 5/1999 | Arndt et al. | |
| 5,941,849 A * | 8/1999 | Amos et al. | 604/95.04 |
| 6,159,177 A * | 12/2000 | Amos et al. | 604/95.04 |
| 6,165,183 A * | 12/2000 | Kuehn et al. | 606/139 |
| 6,231,542 B1 | 5/2001 | Amos et al. | |
| 6,358,271 B1 | 3/2002 | Egan et al. | |
| 6,454,740 B1 * | 9/2002 | Mody | 604/95.04 |
| 6,508,789 B1 * | 1/2003 | Sinnott et al. | 604/164.02 |
| 6,547,761 B2 | 4/2003 | Liu | |
| 6,673,060 B1 | 1/2004 | Fleming, III | |
| 6,699,233 B2 | 3/2004 | Slanda et al. | |
| 7,087,038 B2 | 8/2006 | Lee | |
| 7,217,256 B2 * | 5/2007 | Di Palma | 604/104 |
| 7,578,814 B2 | 8/2009 | Accisano, III et al. | |
| 2004/0059293 A1 | 3/2004 | Chu et al. | |
| 2005/0070821 A1 | 3/2005 | Deal et al. | |
| 2005/0107739 A1 | 5/2005 | Palma | |
| 2005/0203485 A1 | 9/2005 | Lee | |
| 2006/0212009 A1 | 9/2006 | Accisano et al. | |
| 2006/0217667 A1 | 9/2006 | Accisano et al. | |
| 2007/0032779 A1 | 2/2007 | Accisano et al. | |
| 2007/0083189 A1 | 4/2007 | Lampropoulos | |
| 2008/0097394 A1 | 4/2008 | Lampropoulos | |

FOREIGN PATENT DOCUMENTS

| | | |
|---|---|---|
| WO | WO 2006/098819 | 9/2006 |
| WO | WO 2006/101592 | 9/2006 |
| WO | WO 2007/019074 | 2/2007 |

OTHER PUBLICATIONS

International Search Report and Written Opinion, PCT/US06/03021, mailed Sep. 18, 2007, Accisano et al.

International Search Report and Written Opinion, PCT/US06/03464, mailed Jul. 26, 2007, Accisano et al.

International Search Report and Written Opinion, PCT/US06/03467, mailed Jun. 14, 2006, Accisano et at.

International Search Report and Written Opinion, PCT/US06/29304, mailed Feb. 21, 2007, Accisano et al.

Office Action issued May 28, 2008 in co-pending U.S. Appl. No. 11/078,140.

Interview Summary issued Nov. 25, 2008 in co-pending U.S. Appl. No. 11/078,140.

Amendment and Response to Office Action filed Nov. 26, 2008 in co-pending U.S. Appl. No. 11/078,140.

Statement of Substance of Interview filed Dec. 22, 2008 in co-pending U.S. Appl. No. 11/078,140.

Final Office Action issued Mar. 3, 2009 in co-pending U.S. Appl. No. 11/078,140.

Interview Summary issued Jul. 7, 2009 in co-pending U.S. Appl. No. 11/078,140.

Amendment After Final and RCE filed Sep. 3, 2009 in co-pending U.S. Appl. No. 11/078,140.

Office Action issued Sep. 4, 2008 in co-pending U.S. Appl. No. 11/198,642.

Amendment and Response filed Dec. 19, 2008 in co-pending U.S. Appl. No. 11/198,642.

Interview Summary issued Dec. 23, 2008 in co-pending U.S. Appl. No. 11/198,642.

Statement of Substance of Interview filed Jan. 23, 2009 in co-pending U.S. Appl. No. 11/198,642.

Notice of Allowance issued Apr. 20, 2009 in co-pending U.S. Appl. No. 11/198,642.

Issue Notification issued Aug. 5, 2009 in co-pending U.S. Appl. No. 11/198,642.

Request for Continued Examination filed Aug. 24, 2009 in co-pending U.S. Appl. No. 11/198,642.

Final Office Action issued Mar. 10, 2009 in co-pending U.S. Appl. No. 11/081,301.

Amendment and Response filed Dec. 29, 2008 in co-pending U.S. Appl. No. 11/081,301.

Office Action issued Jun. 26, 2008 in co-pending U.S. Appl. No. 11/081,301.

Amendment filed Apr. 23, 2008 in co-pending U.S. Appl. No. 11/081,301.

Office Action issued Oct. 23, 2007 in co-pending U.S. Appl. No. 11/081,301.

Office Action issued Oct. 16, 2008 in co-pending U.S. Appl. No. 11/608,518.

Interview Summary issued Mar. 31, 2009 in co-pending U.S. Appl. No. 11/608,518.

Amendment and Response filed Apr. 16, 2009 in co-pending U.S. Appl. No. 11/608,518.

Notice of Allowance issued Jul. 27, 2009 in co-pending U.S. Appl. No. 11/608,518.

Office Action issued May 6, 2009 in co-pending U.S. Appl. No. 11/507,777.

Interview Summary issued Jul. 17, 2009 in co-pending U.S. Appl. No. 11/507,777.

Amendment and Response filed Aug. 6, 2009 in co-pending U.S. Appl. No. 11/507,777.

* cited by examiner

DRAINAGE CATHETER HUB WITH WELDED SUTURE AND SIDEWALL STYLET

BACKGROUND OF THE INVENTION

1. The Field of the Invention

The present invention relates to catheters. In more particular, the present invention relates to a drainage catheter hub having a welded suture and a stylet lumen in the sidewall of the drainage catheter tubing. The suture and stylet are adapted to secure a suture thread to maintain the anchor configuration of the distal end of the catheter in order to secure the position of the catheter within the patient's body.

2. The Relevant Technology

Drainage catheters are utilized to drain volumes of fluids that collect in a patient's tissue, body cavities, or other positions within a patient's body that exceed normal volumes. Collected fluids can contribute to infection, exert harmful pressure on the patient's organs, or otherwise impede with proper care and recovery of a patient. The drainage catheter is introduced into the patient to the site where the excess fluid is accumulated. A plurality of drainage bores are positioned in the distal end of the catheter to allow passage of the fluids from the volume of fluid to the lumen of the catheter.

FIG. 1 is a perspective view of a prior art drainage catheter tube 10. Distal end 14 of drainage catheter tube 10 is adapted to be positioned in a volume of fluid to be drained from a patient. In the illustrated embodiment, distal end 14 is curved to form an anchor configuration to secure the drainage catheter at the site where excess fluid is accumulated. Loop 16 comprises the anchor configuration formed in distal end 14. The configuration of loop 16 provides a reliable anchor even in the event that the tissue surrounding the drainage site does not provide a solid or reliable substrate to maintain the position of the catheter. Loop 16 is formed by curling distal end 14 of catheter tube 10 such that the tip of the catheter tube 10 contacts a more proximal position on catheter tube 10. Suture 18 is utilized to form loop 16 to anchor distal end 14 in a desired drainage position. Suture 18 runs the length of catheter tube 10 such that it extends from a proximal end of catheter tube 10. Because the proximal end of catheter tube 10 is configured to be positioned outside the patient, suture 18 allows a user to secure or release loop 16 once the distal end 14 of catheter tube 10 is positioned inside the patient.

A plurality of drainage bores 20 are formed on the inside diameter of loop 16. Drainage bores 20 allow fluid to flow from the volume of fluid in the body cavity to a lumen 22 of catheter tube 10. A stylet 24 is provided to selectively secure suture 18 such that suture 18 can be utilized to form loop 16. Loop 16 is formed by securing the tip of catheter tube 10 to a point on catheter tube 10 corresponding with a suture bore 23. Suture 18 runs the length of lumen 22, exits the tip of catheter tube 10, enters suture bore 23, and is wrapped around stylet 24. Stylet 24 is positioned in a stylet lumen 26 in catheter wall 28. Stylet lumen 26 and stylet 24 terminate at suture bore 23 adjacent the distal end 14. When suture 18 is provided with sufficient slack, distal end 14 of catheter tube 10 can be straightened for insertion or removal of distal end 14 to/from the patient. When suture 18 is foreshortened, the tip of catheter tube 10 is securely drawn to a position on catheter tube 10 corresponding with suture bore 23. When tip of catheter tube 10 is secured adjacent suture bore 23, loop 16 is formed.

Suture 18 is adapted to have a double length configuration along the length of lumen 22 such that both ends of suture 18 extend from the proximal end (not shown) of catheter tube 10. In other words, suture 18 is threaded distally along the length of lumen 22 of catheter tube 10, exits catheter tube 10, is wrapped around stylet 24, re-enters catheter tube 10, and is threaded back to the proximal end of the catheter tube 10. The user manipulates both ends of suture 18 to tighten or loosen the anchor configuration of distal end 14. To tighten the anchor configuration the user grasps both ends of suture 18 and pulls in a rearward direction. To loosen the anchor configuration of distal end 14, the user relaxes the tension on, or releases, both ends of suture 18. Because suture 18 secures distal end 14 while extending to the proximal end of catheter tube 10, the user can manipulate suture 18 to maintain or release the anchor configuration of the distal end 14 of the catheter tube 10 while the distal end 14 of the catheter tube 10 is positioned inside the patient. In one device one end of the suture is anchored relative to the catheter hub while the other end is free.

When the volume of fluid in the body cavity of the patient has been drained, the practitioner will release loop 16 such that catheter tube 10 is no longer anchored in the body cavity. By releasing loop 16, catheter tube 10 can be removed from the patient. The user can release loop 16 utilizing one, or both, of suture 18 and stylet 24. To release loop 16 utilizing stylet 24, a user simply retracts stylet 24 in a rearward direction. Because suture 18 is secured to catheter tube 10 by stylet 24, once stylet 24 is retracted beyond suture bore 23, nothing is available to secure suture 18 to catheter tube 10. As a result, suture 18 is released and catheter tube 10 can be withdrawn from the patient.

The practitioner can also utilize suture 18 to release loop 16 and withdraw catheter tube 10 from the patient without retracting stylet 24. To release loop 16 utilizing suture 18, the user grasps only one of the two ends of suture 18 that is extended from the proximal end (not shown) of catheter tube 10. The user then pulls the end of suture 18 in a rearward direction. This pulls the free end of suture 18 into catheter tube 10. As the user continues to pull the end of suture 18 in a rearward direction, the free end of suture 18 travels the length of lumen 22, exits the tip of catheter tube 10, and is unwound from stylet 24. Once suture 18 is unwound from stylet 24 the tip of catheter tube 10 is no longer secured adjacent the proximal position on catheter tube 10 and loop 16 is released. The practitioner can utilize suture 18 in the event that stylet 24 becomes bound by tissue, is kinked, or otherwise becomes inoperable. The practitioner can also utilize the double length configuration of suture 18 to release loop 16 in drainage catheter designs that do not include a stylet.

One drawback presented by the double length configuration of suture 18 relates to the passage of fluids through drainage bores 20. In the illustrated embodiment, the double length of suture 18 is depicted as being positioned in the center of lumen 22 along the entire length of catheter tube 10. This positioning is provided to more clearly illustrate the double length configuration of suture 18. In practice, the tension on suture 18 utilized to maintain the configuration of loop 16 draws suture 18 against the inner diameter of lumen 22. This positions suture 18 across drainage bores 20 substantially reducing the effective cross-section of drainage bores 20. As a result, a lesser amount of volume is permitted to pass from the exterior of catheter tube 10 to lumen 22. Additionally, larger articles and materials such as clots, tissue, or other materials suspended in the fluid cannot be drained through the drainage bores. This not only makes drainage of fluids less efficient, it also increases the likelihood that the drainage bores 20 will be clogged by materials suspended in the fluid.

FIG. 1B illustrates a prior art drainage catheter tube 10a which overcomes some of the deficiencies presented by the design of drainage catheter tube 10 of FIG. 1A. In the illustrated embodiment, a suture 18 having a single length is provided in connection with drainage catheter tube 10a. Suture 18 does not extend to the tip of catheter tube 10a. Instead, suture 18 exits catheter wall 28 at a position proximal to the tip of catheter tube 10a. In contrast to catheter tube 10 of FIG. 1A, stylet 24a and stylet lumen 26a extend along the inside diameter of loop 16a to approximately the tip of catheter tube 10a. Suture 18 extends from an exit bore 29 positioned proximally on catheter tube 10a through catheter wall 28 and around stylet 24. Suture 18 is secured to stylet 24 by tying a knot in the distal end of suture 18. This allows the use of a single length design for suture 18 minimizing obstruction along the length of lumen 22. Because stylet 24a and stylet lumen 26a extend along the inside diameter of loop 16a, drainage bores 20a are positioned on the outside diameter of loop 16a. This permits drainage of fluid to lumen 22 through drainage bores 20a without obstruction from suture 18 or stylet 24a.

While the design of drainage catheter tube 10a overcomes some of the deficiencies of catheter tube 10 of FIG. 1A, catheter tube 10a also has a number of deficiencies. For example, the knot formed in the distal end of suture 18 utilized to secure suture 18 to stylet 24a can be easily encrusted with clots, tissue, or other materials suspended in the fluid. This encrustation can lodge suture 18 within stylet lumen 26a such that when stylet 24a is removed, suture 18 and loop 16a are not released. This can be problematic, particularly where the practitioner is unaware that the anchor configuration of loop 16a has not been released and attempts to withdraw the catheter.

Another deficiency is presented by the positioning of drainage bores 20a on the outside diameter loop 16a. In some clinical settings, when the volume of fluid begins to drain, the positive pressure on the walls of the cavity in which drainage catheter tube 10a is positioned begins to decrease. This can result in shrinking of the size of the cavity. As the size of the cavity begins to shrink, the walls of the cavity contact the outside diameter of loop 16a. This can result in obstruction of drainage bores 20a directly by the walls of the cavity before the volume of fluid in the cavity is sufficiently drained. Where the practitioner relies on the volume of fluid being drained from the proximal end of the catheter as an indicator of the volume of fluid in the cavity, the practitioner may believe that no additional fluid is contained in the cavity. Additionally, the practitioner may be unaware of recurring fluid draining into the cavity that may otherwise be drained if not for blocking of the drainage bores 20a by the cavity wall. As a result, when the flow of fluid slows or stops prematurely in a particular procedure as a result of contact between the drainage bores 20a and the cavity walls, the practitioner may prematurely withdraw the drainage catheter tube 10a from the patient.

BRIEF SUMMARY OF THE INVENTION

The present invention relates to catheters. In more particular, the present invention relates to a drainage catheter having a welded suture configuration to secure the distal end of the catheter in an anchor configuration. In one embodiment, the suture is welded into a loop at the distal end of the suture to secure the anchor configuration of the distal end of the catheter. For example, the suture can be threaded through a first bore in catheter wall at the tip of the catheter and exit a second bore in the catheter wall. The tip of the suture can then be welded back to the length of suture that has not yet entered the catheter wall. In another embodiment, the welded suture is utilized to form a loop that secures the suture to a stylet positioned in the catheter wall. In one illustrative embodiment, the suture is welded utilizing a single strand weld. In another embodiment, the suture is welded utilizing a multiple strand weld.

The present invention also relates to a drainage catheter having a plurality of drainage bores positioned on the inside diameter of the anchor loop to provide advantageous draining of fluid into the lumen of the catheter. In one embodiment of the present invention, the drainage catheter includes a stylet and stylet lumen positioned in the sidewall of the catheter approximately 90 degrees from the inside diameter of the drainage bores. By positioning the stylet and stylet lumen in the sidewall of the catheter, the drainage bores on the inside diameter of the drainage catheter can operate without obstruction from the stylet and suture. In one embodiment, the suture extends to tip of the catheter and is secured by the stylet which terminates proximally to the distal end of the catheter. In another embodiment, the stylet extends to the tip of the catheter and the suture exits the catheter proximally to the distal end of the catheter. In this embodiment, the suture is secured to the catheter tip by the stylet.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to catheters. In more particular, the present invention relates to a drainage catheter having a weld to secure the distal end of the catheter in an anchor configuration. In one embodiment, the suture is welded into a loop at the distal end of the suture to secure the anchor configuration of the distal end of the catheter. In another embodiment, the welded suture is utilized to form a loop that secures the suture to the stylet positioned in the catheter wall. In one illustrative embodiment, the suture is welded utilizing a single strand weld. In another embodiment, the suture is welded utilizing a multiple strand weld.

The present invention also relates to a drainage catheter having a plurality of drainage bores positioned on the inside diameter of the anchor loop to provide advantageous draining of fluid into the lumen of the catheter. In one embodiment of the present invention, the drainage catheter includes a stylet and stylet lumen positioned in the sidewall of the catheter approximately 90 degrees from the inside diameter of the catheter tube and drainage bores. By positioning the stylet and stylet lumen in the sidewall of the catheter, the drainage bores on the inside diameter of the drainage catheter can operate without obstruction from the stylet and suture.

Figure 1A:
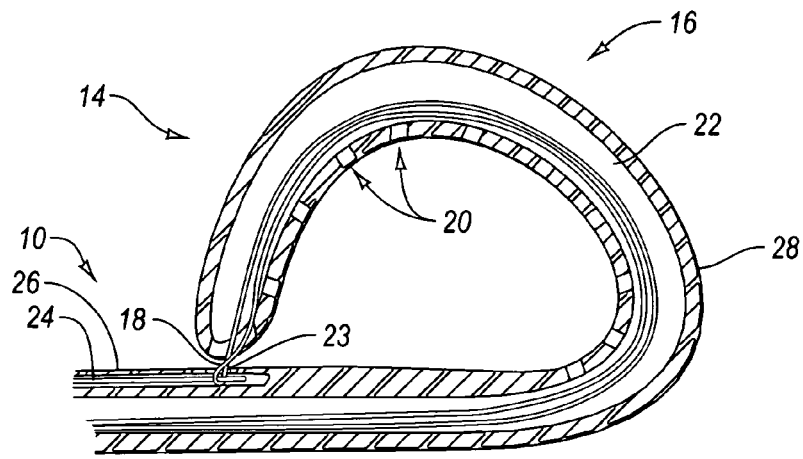
FIG. 1A is a cross-section of a prior art drainage catheter tube having a double length suture for maintaining the anchor configuration of the distal end of the catheter.
Figure 1B:
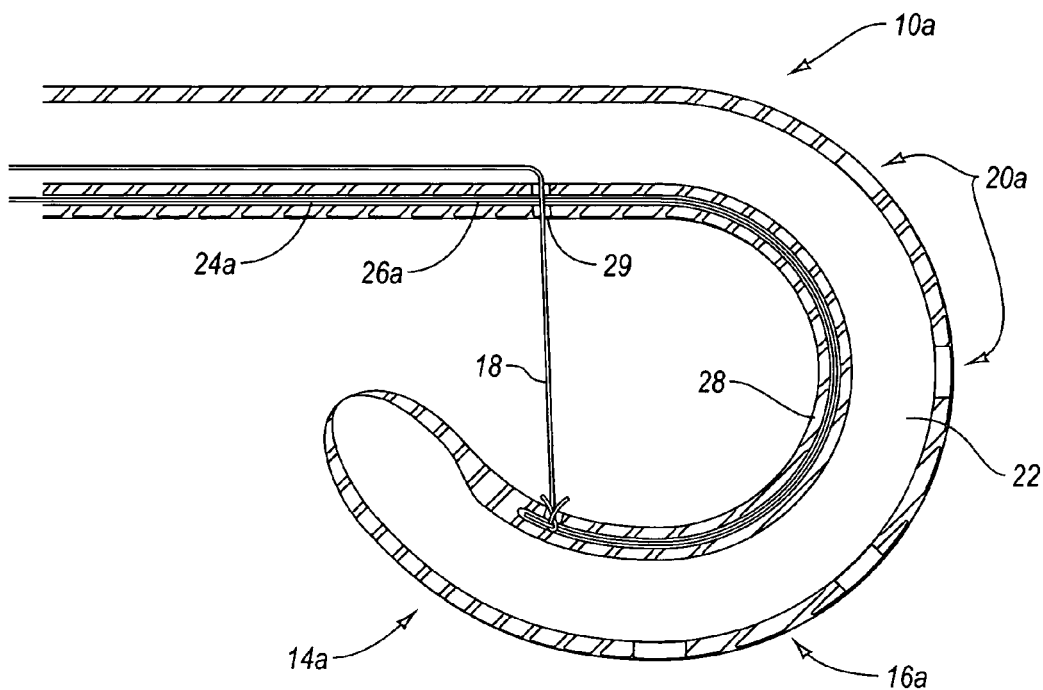
FIG. 1B is a cross-section of a prior art drainage catheter tube having a plurality of drainage bores on the outside diameter of the distal end of the catheter.
Figure 2:
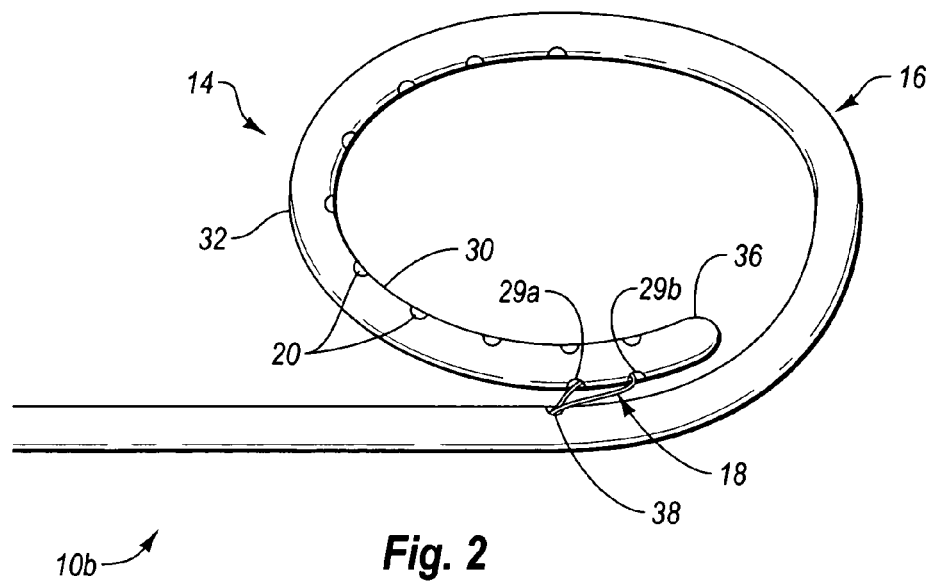
FIG. 2 is a side view of a drainage catheter tube having a welded suture for maintaining the anchor configuration of the distal end of the catheter.
Figure 3:
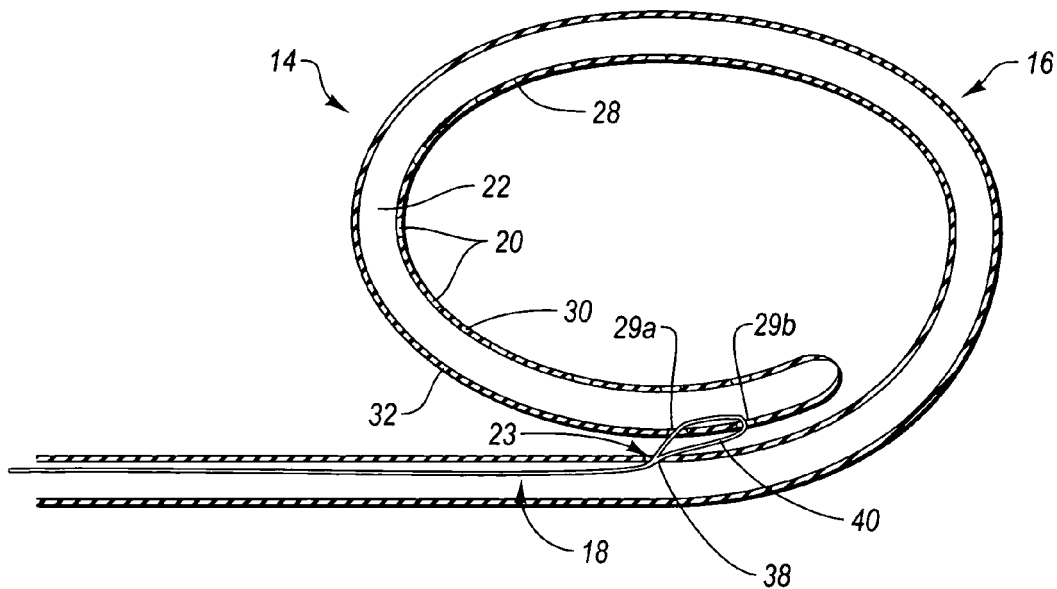
FIG. 3 is a cross-section of the drainage catheter tube of FIG. 2 according to one embodiment of the present invention.

FIGS. 2 and 3 are perspective views of the drainage catheter tube 10b according to one embodiment of the present invention. In the illustrated embodiment, drainage catheter tube 10b includes a distal end 14, a suture 18, and a plurality of drainage bores 20. Catheter tube 10b comprises an elongate hollow tube configured to permit the passage of fluids from a patient. Distal end 14 of drainage catheter tube 10b is configured to form loop 16 to provide anchoring of the drainage catheter tube 10b within a volume of fluid to be drained from a patient. The plurality of drainage bores 20 are positioned in distal end 14 of catheter tube 10b. Drainage bores 20 allow for passage of fluid from the body cavity of the patient to lumen 22 of catheter tube 10b. Suture 18 allows the user to secure the anchor configuration of distal end 14. The anchor configuration of distal end 14 secures the drainage catheter tube 10b in a desired drainage position within the patient.

In the illustrated embodiment, suture 18 extends along the length of catheter lumen 22 in a single length configuration. Suture 18 exits lumen 22 at a suture bore 23 positioned in catheter wall 28. Suture bore 23 is positioned proximally to the distal end 14 of catheter tube 10b. Suture 18 secures the tip of catheter tube 10b adjacent the suture bore 23 to form the anchor configuration of loop 16. Suture 18 is secured to the distal end 14 of catheter by being threaded through bores 29a and 29b. Bores 29a and 29b are positioned adjacent the tip of distal end 14. When the practitioner increases the tension on suture 18, bores 29a and 29b are drawn adjacent suture bore 23 on catheter tube 10b.

In the illustrated embodiment, suture 18 includes a weld 38. Weld 38 secures one portion of suture 18 to a second portion of suture 18 to secure the loop configuration in the distal end of suture 18. In one embodiment, suture 18 comprises a monofilament nylon or other polymer filament line. Weld 38 is formed by first positioning two lengths of the monofilament line comprising suture 18 adjacent one another. Typically, the two lengths of monofilament line are positioned in parallel such that the two lengths are in contact along a length of the line. Once the two lengths of the monofilament line comprising suture 18 are correctly positioned, ultrasonic energy is applied to suture 18. The ultrasonic energy provides a reliable and unobtrusive securing of the two lengths to one another.

Weld 38 results in a smooth integration of one portion of suture 18 to a second portion of suture 18. Weld 38 eliminates or minimizes enlarged structures and loose ends on suture 18 that can result from alternative securement designs. The unobtrusive configuration of weld 38 minimizes snagging of the distal end of suture 18 during operation of suture 18. Weld 38 provides a simple, effective, and unobtrusive mechanism for utilizing a single suture length design while effectively securing distal end of suture 18 to distal end 14 of catheter tube 10b. In one embodiment of the present invention a weld of the suture is utilized in connection with a knot to provide for more reliable securement of one portion of the suture to another portion of the suture.

The design of suture 18 allows positioning of drainage bores 20 on the inside diameter 30 of loop 16 without obstruction from suture 18. The pathway of suture 18 allows securing of distal end 14 without passing through the portion of lumen 22 coterminous with drainage bores 20. As a result, drainage bores 20 can be positioned on the inside diameter 30 of loop 16 without being covered by suture 18. Placement of drainage bores 20 on the inside diameter 30 of loop 16 allows drainage of fluid even where an outside diameter 32 of loop 16 is contacted by the walls of the body cavity. The ability to drain fluid where the walls of the body cavity contact the outside diameter 32 can be helpful where recurring fluids drain into a relatively small body cavity. It can also be helpful where the drainage of fluids results in shrinkage of the body cavity due to decreased pressure being exerted on the body cavity walls from the fluids.

Because suture 18 does not pass over drainage bores 20, the effective cross-section of drainage bores 20 is increased by up to more than 100%. Increasing the effective cross-section of drainage bores 20 facilitates efficient draining of fluid into lumen 22 of catheter tube 10b. Additionally, increasing the effective cross-section of drainage bores 20 allows the passage of clots, tissue, and other materials that are often suspended in fluids to be drained. Because suture 18 does not pass over drainage bores 20, such clots, tissue, and other materials are not caught on suture 18 while passing into drainage bores 20. Because such clots, tissue, and other materials are not caught on suture 18, additional buildup of materials is minimized. This substantially slows or prevents clogging of individual drainage bores. As a result, the time in which drainage catheter tube 10b can provide reliable draining is substantially increased. This allows drainage catheter tube 10b to remain in the patient for longer periods without requiring replacement. Because the practitioner can leave the drainage catheter in place for longer periods of time, the number of times the drainage catheter must be removed and replaced during a long term drainage procedures is decreased. By decreasing the number of times the drainage catheter must be removed and replaced, the potential for complications that can occur during removal and placement of the catheter is also substantially decreased.

The inclusion of weld 38 in suture 18 provides reliable and unobtrusive securement of suture 18 while utilizing a single length suture design. The presence of a single suture length inside lumen 22 minimizes obstruction to the flow of fluids and other articles and materials suspended in the fluid. Additionally, utilizing the single suture length minimizes the possibility that clots, tissue, or other articles or materials will attach to suture 18 thereby preventing effective passage of fluids and materials through lumen 22 of catheter tube 10b. Suture 18 also allows the use of monofilaments having increased solid surface bearing qualities or other non-slip characteristics. Such solid surface bearing qualities can help prevent the attachment of clots, tissue, and other materials to suture 18 along the length of lumen 22.

Figure 4:
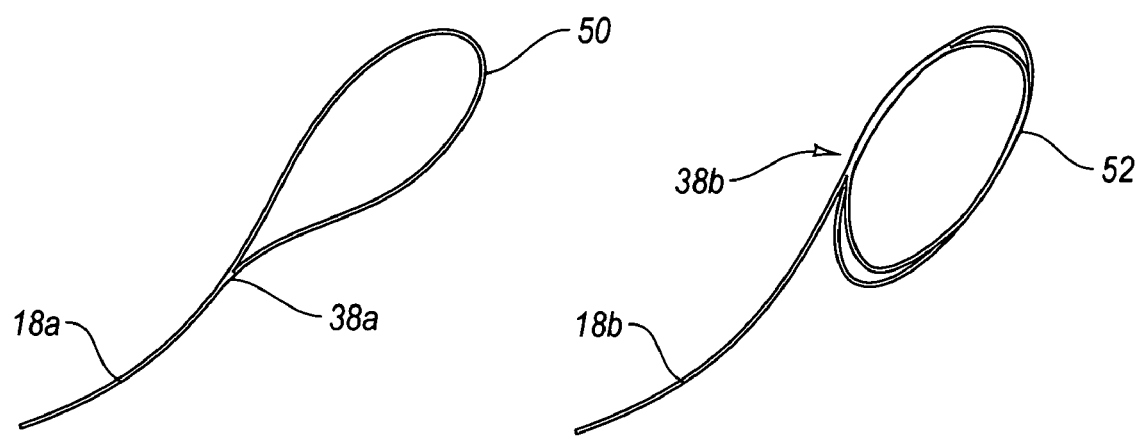
FIG. 4 illustrates welded sutures having a single loop and double loop configuration according to one embodiment of the present invention.

FIG. 4 is a perspective view of suture 18*a* having a single weld 38*a* and suture 18*b* having a double weld 38*b*. In the illustrated embodiment, suture 18*a* includes a single loop 50 positioned at the distal end of suture 18*a*. Single weld 38*a* provides securement of the tip of suture 18*a* to a proximally positioned length of suture 18*a*. To form single weld 38*a*, a length of the tip of suture 18*a* is positioned in parallel and in contact with a proximally positioned length of suture 18*a*. The two lengths of suture 18*a* are positioned so as to leave a single loop 50 remaining between the two lengths. Ultrasonic energy is then applied to the two lengths of suture 18*a* while forcing the two lengths of suture 18*a* together. The resulting single weld 38*a* provides both a reliable and unobtrusive design. Additionally, weld 38*a* permits the use of a greater variety of monofilament or other materials for suture 18*a*.

In the illustrated embodiment, suture 18*b* includes a double loop 52 positioned at the distal end 14 of suture 18*b*. Double loop 52 provides a double length securement of the tip of a drainage catheter tube 10. The double length design of double loop 52 provides additional strength for securing the tip of the drainage catheter tube 10. Additionally, in the event that one loop of the double loop 52 fails as a result of strain, abrasion, or other factors, another loop is available to continue to retain the tip of the catheter tube 10.

To form double weld 38*b*, the distal end of suture 18*b* is looped such that two lengths of suture 18*b* are positioned in parallel and in contact with one another. A second loop is then formed such that the distal end of suture 18*b* is positioned in parallel and in contact with the first two portions of suture 18*b* that were previously placed in contact with one another. Ultrasonic energy is then applied to the three lengths of suture while forcing the three lengths of suture 18*b* together. The resulting double weld design 38*b* provides a strong, reliable, and unobtrusive design while allowing the use of a greater variety of monofilament or other materials for suture 18*b*.

As will be appreciated by those skilled in the art, a variety of types and configurations of welds can be utilized with the suture without departing from the scope and spirit of the present. For example, in one embodiment a weld is utilized to secure two separate sutures together. In another embodiment, the suture is welded to a secondary member to secure the suture to the catheter tube. In another embodiment, a suture weld is utilized to provide a triple loop design. In another embodiment, two or more welds are provided to form the loop at the distal end of the suture. In yet another embodiment, the weld is formed utilizing a weld mechanism other than ultrasonic energy. For example, the weld can be formed utilizing an adhesive, thermally bonding, fusing, chemically, or through other bonding process or mechanism.

Figure 5A:
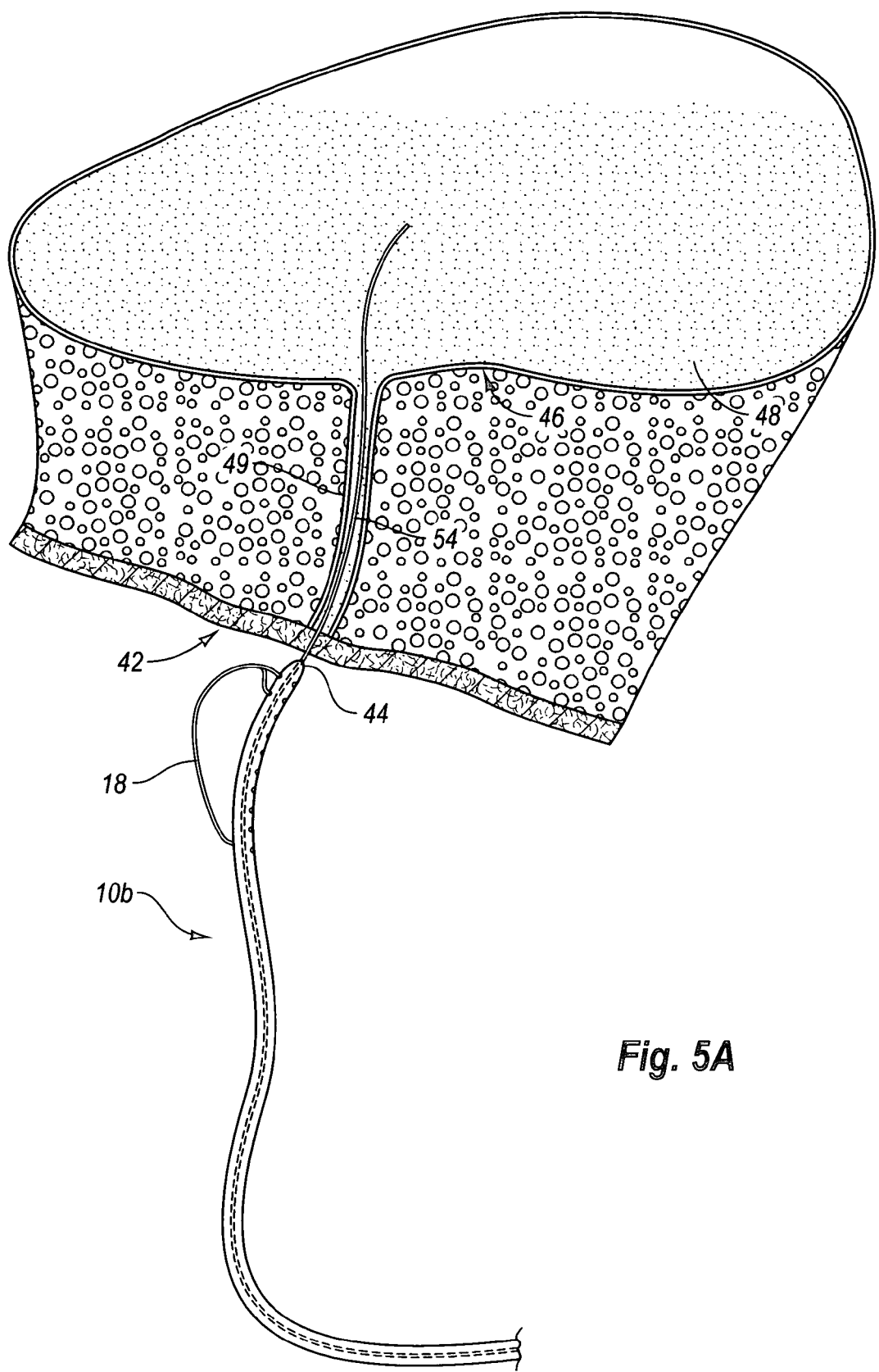
FIG. 5A illustrates a drainage catheter tube in preparation to be inserted into a body cavity of a patient utilizing a guidewire.

FIG. 5A illustrates a drainage catheter tube 10*b* in preparation for being inserted into a body cavity 46 of a patient 42. In the illustrated embodiment, a volume of fluid 48 is contained within a body cavity 46 of patient 42. While fluid 48 is depicted as being uniform in nature for the sake of clarity, it will be appreciated that it is not unusual for bodily fluid to include blood clots, tissue, and other materials. The presence of such materials can result from the nature of the fluid, infection, a medical condition of the patient, internal injury, or other medical complication.

A guidewire 54 is threaded into the volume of fluid 48 through a channel 49. Channel 49 can be created as part of the drainage catheter tube 10*b* placement procedure. Channel 49 can also be a naturally existing channel such as a bodily orifice, patient vasculature, or the result of an injury or natural occurrence. Catheter tube 10*b* is threaded over guidewire 54 in preparation for being introduced into body cavity 46 through channel 49. Suture 18 is provided with sufficient slack to permit straightening of distal end 14 of catheter tube 10*b*. When distal end 14 of catheter tube 10*b* is in a straightened configuration, tip 44 of catheter tube 10*b* is positioned to be inserted into channel 49.

Figure 5B:
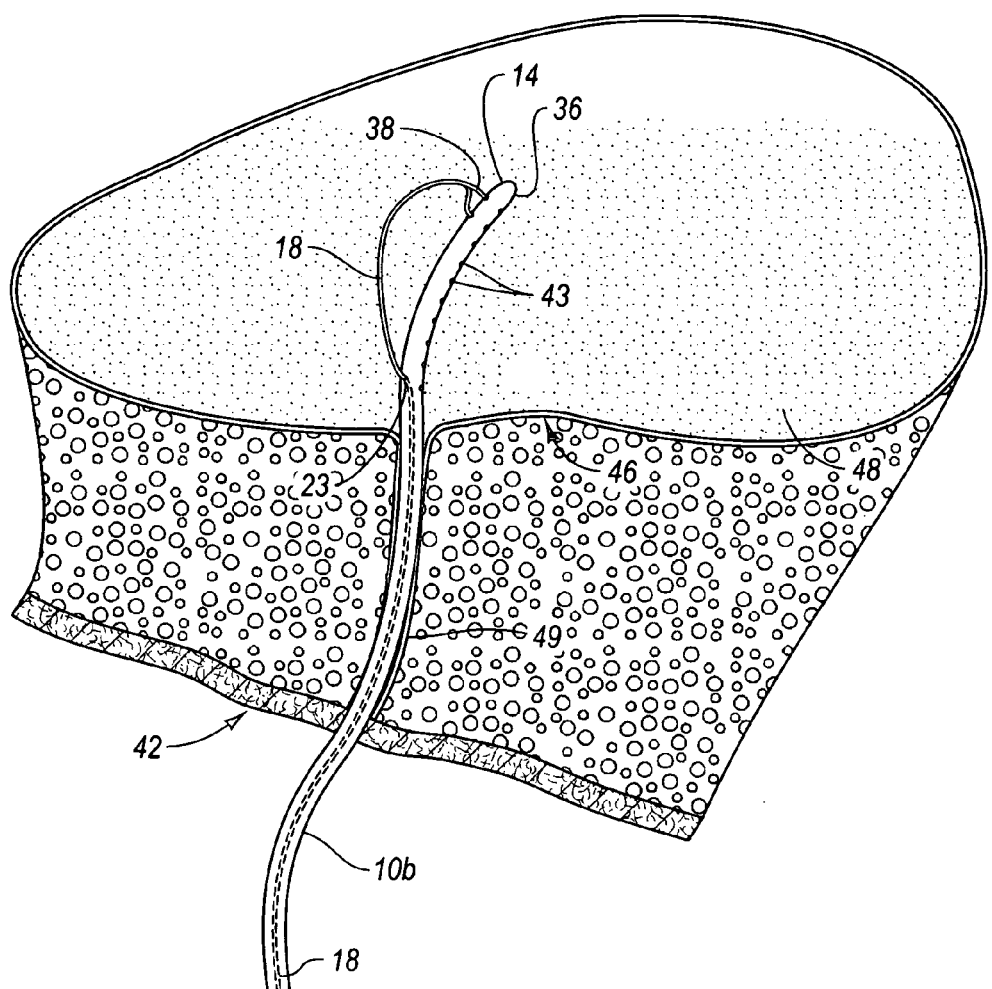
FIG. 5B illustrates the drainage catheter tube of FIG. 5A being inserted into a patient.
Figure 5B:
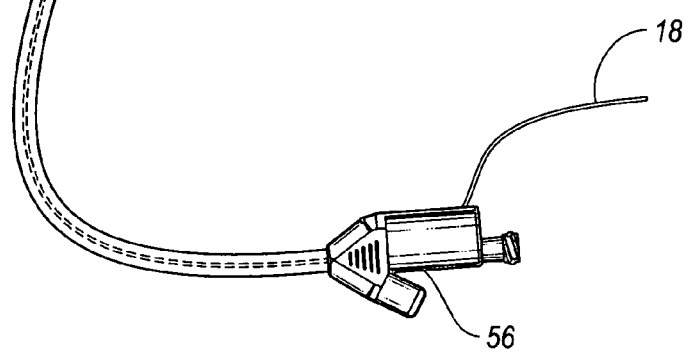

FIG. 5B is a cross-sectional view of patient 42 illustrating drainage catheter tube 10*b* subsequent to being introduced into body cavity 46 of patient 42. In the illustrated embodiment, guidewire 54 (depicted in FIG. 5A) has been withdrawn from the patient 42. Distal end 14 is in a substantially straightened configuration. As previously discussed, suture 18 is utilized to form the anchor configuration of distal end 14. Suture 18 is secured to tip 44 of catheter tube 10*b* utilizing weld 38.

The slack in suture 18 is depicted as forming a loop extending adjacent the length of distal end 14. In practice, suture 18 will closely contact the outside surface of distal end 14 to minimize snagging of suture 18 during insertion through channel 49. Suture 18 is threaded along the length of the lumen of catheter tube 10*b* from suture bore 23 to a hub 56. The path of suture 18 along the length of catheter tube 10*b* is depicted in phantom lines. Suture 18 exits hub 56 and extends proximally allowing a user to grasp and manipulate the proximal portion of suture 18. The user can release the tension on the proximal portion of suture 18 to allow straightening of distal end 14 as depicted in the illustrated embodiment.

Figure 5C:
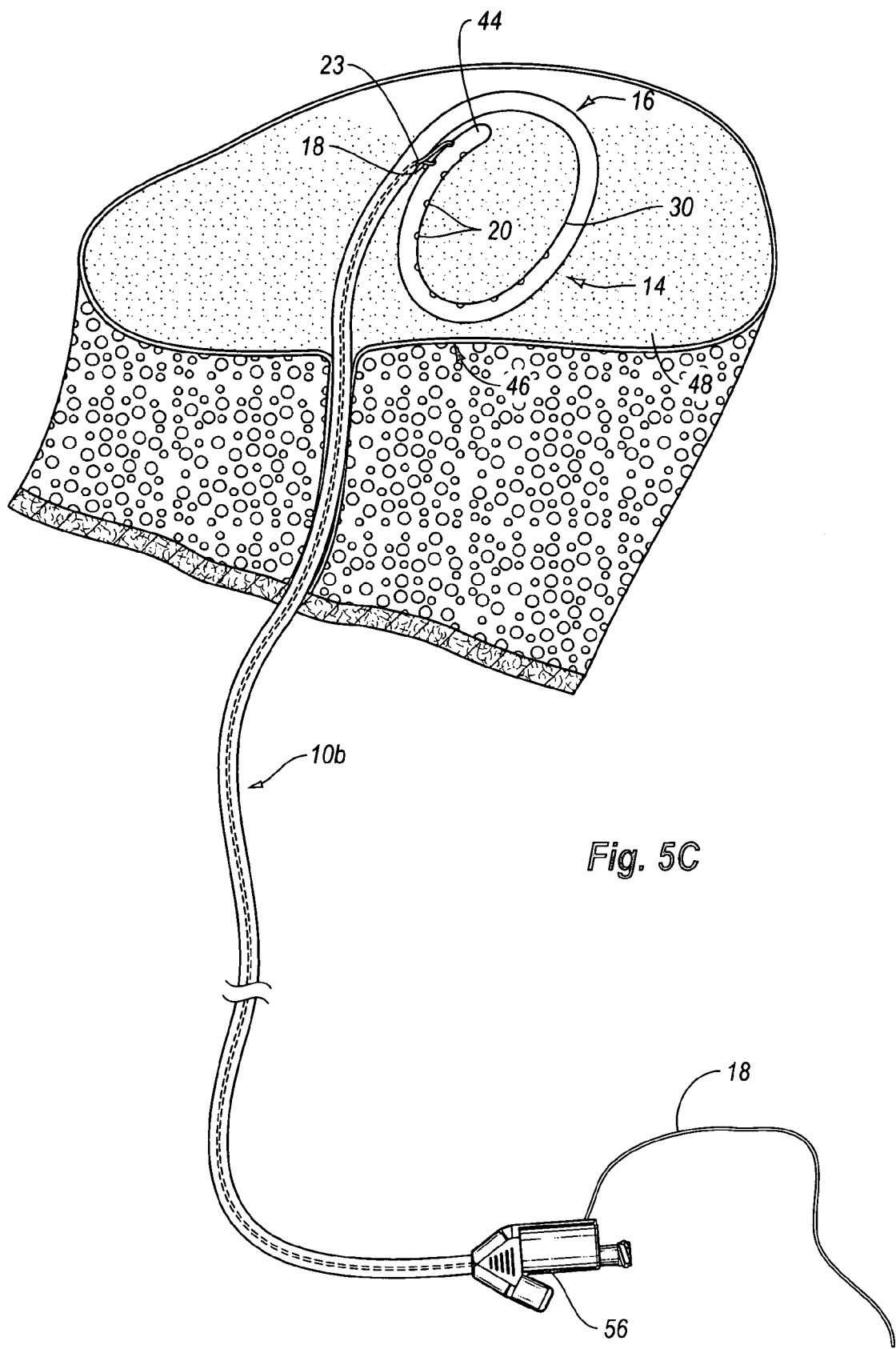
FIG. 5C illustrates the drainage catheter tube of FIG. 5A with the distal end of the drainage catheter tube being positioned in an anchor configuration.

FIG. 5C depicts distal end 14 formed in a loop 16 to anchor catheter tube 10*b* in body cavity 46. Loop 16 has an enlarged pig-tail type configuration to provide a large surface contact area and reliable anchoring even where the wall of body cavity 46 does not provide a reliable securement substrate. As a result, inadvertent or unintentional pulling of catheter tube 10*b* does not change the drainage position of distal end 14 of catheter tube 10*b*. When loop 16 contacts the wall of body cavity 46, a sufficient contact area is provided that loop 16 does not damage the wall of body cavity 46. Additionally, loop 16 can be flexed or stretched to alleviate and diffuse pressure exerted on one or more points of loop 16.

When distal end 14 forms loop 16, drainage bores 20 are positioned along the inside diameter 30 of loop 16. The positioning of drainage bores 20 along the inside diameter of loop 16 permits efficient and unobstructed drainage of fluid through drainage bores 20 in the event that loop 16 is positioned in contact with a wall of body cavity 46. Fluid 48 is configured to drain from body cavity 46, through drainage bores 20, into and along the length of lumen 22 (not shown) of catheter tube 10*b*, and out the proximal end of catheter tube 10*b*.

Loop 16 is formed utilizing suture 18. In order to form loop 16, the user grasps the proximal portion of suture 18 extending from hub 56. The user then pulls suture 18 in a rearward direction to remove the slack in suture 18 and draw tip 44 into contact with the point where suture 18 is threaded into suture bore 23. The user can then tie or otherwise secure the proximal portion of suture 18 extending from hub 56 to maintain the configuration of loop 16. Once the loop 16 is secured, the practitioner can attend to other aspects of the procedure while drainage of fluid begins. Drainage catheter tube 10*b* can remain in use for recommended periods of time. Such recommended periods can vary based on the manufacturing specifications, type of fluid being drained, and other medical considerations.

Figure 5D:
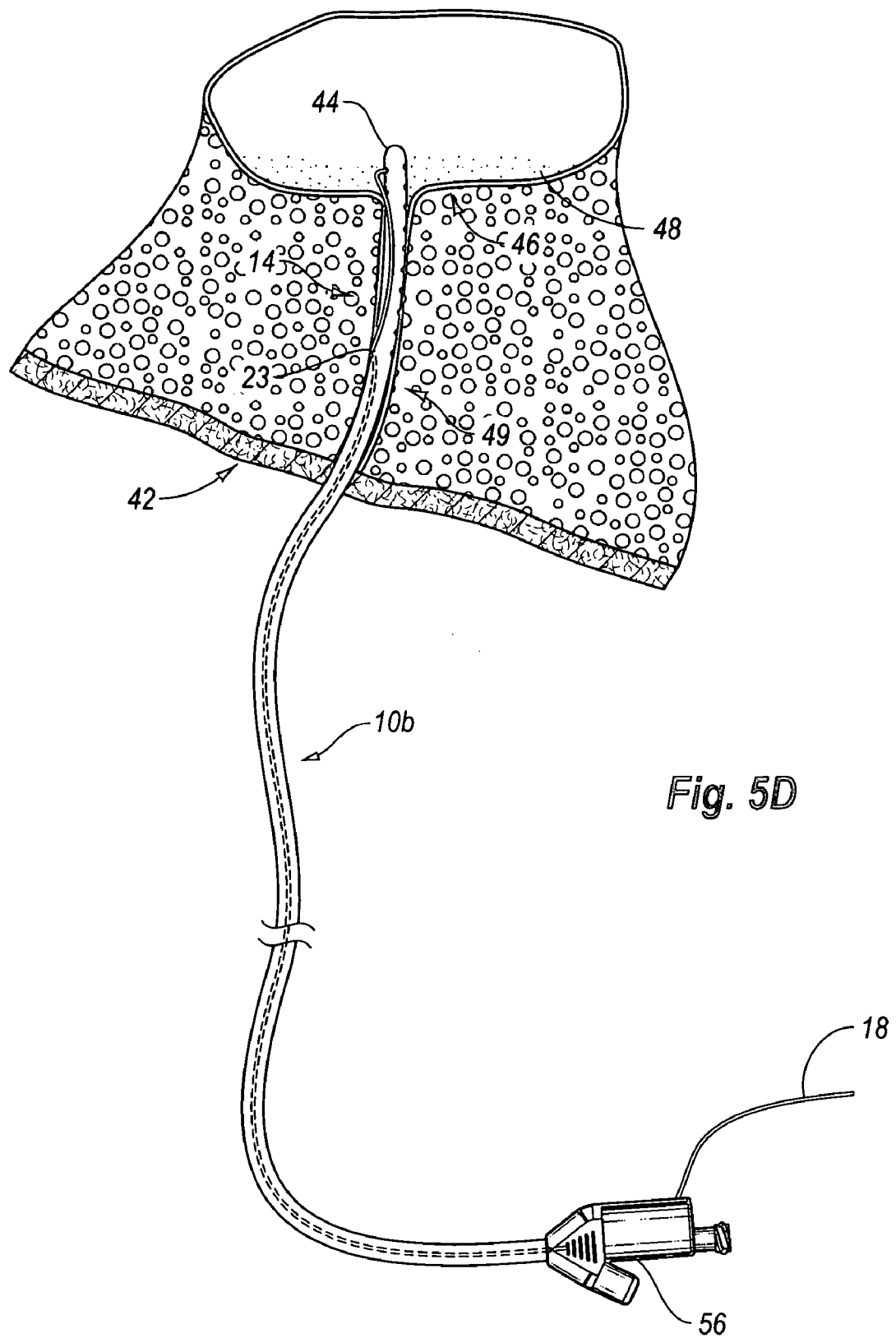
FIG. 5D illustrates the drainage catheter tube of FIG. 5A being removed from a body cavity of a patient subsequent to draining the fluid from the patient.

FIG. 5D illustrates catheter tube 10*b* being withdrawn from patient 42. In the illustrated embodiment, body cavity 46 has been substantially drained of fluid 48. The size of body cavity 46 has also been substantially reduced from the size depicted in FIGS. 5A-5C. The reduced size of body cavity 46 results, at least in part, from the fact that the volume of fluid 48 has been substantially reduced from that depicted in FIGS. 5A-5C. As a result fluid 48 no longer exerts the same amount of outward pressure on the walls of body cavity 46. As previously discussed, the positioning of drainage bores 20 on the inside diameter of loop 16 (not shown) permits draining of bodily fluid even where the size of body cavity 46 is such that the walls of body cavity 46 contact the outside diameter of distal end 14.

To withdraw distal end 14 from body cavity 46, the user first releases the tension on suture 18. Where the proximal end of suture 18 extending from hub 56 has been tied or otherwise secured, the user unties or releases securement of the proximal end of suture 18. The user then releases the tension on suture 18 and begins to retract catheter tube 10b in the rearward direction. As catheter loop 16 (depicted in FIG. 5C) contacts the wall of body cavity 46, pressure on catheter loop 16 (depicted in FIG. 5C) begins to unravel catheter loop 16 (depicted in FIG. 5C). The slack in suture 18 allows movement of tip 44 away from suture bore 23. As a result, distal end 14 can be straightened sufficiently to withdraw catheter tube 10b through channel 49 as depicted.

As will be appreciated by those skilled in the art, a variety of types and configurations of drainage catheter tubes can be utilized to drain a body cavity of a patient without departing from the scope and spirit of the present invention. For example, in one embodiment the drainage catheter tube has a preformed loop configuration that is straightened utilizing a stylet for insertion into the patient. In another embodiment, the drainage catheter tube is anchored to the patient utilizing a securement mechanism in addition to the loop in the distal end of the catheter tube. In another embodiment, the anchor configuration of the distal end of the catheter tube does not form a pig-tail type loop.

Figure 6A:
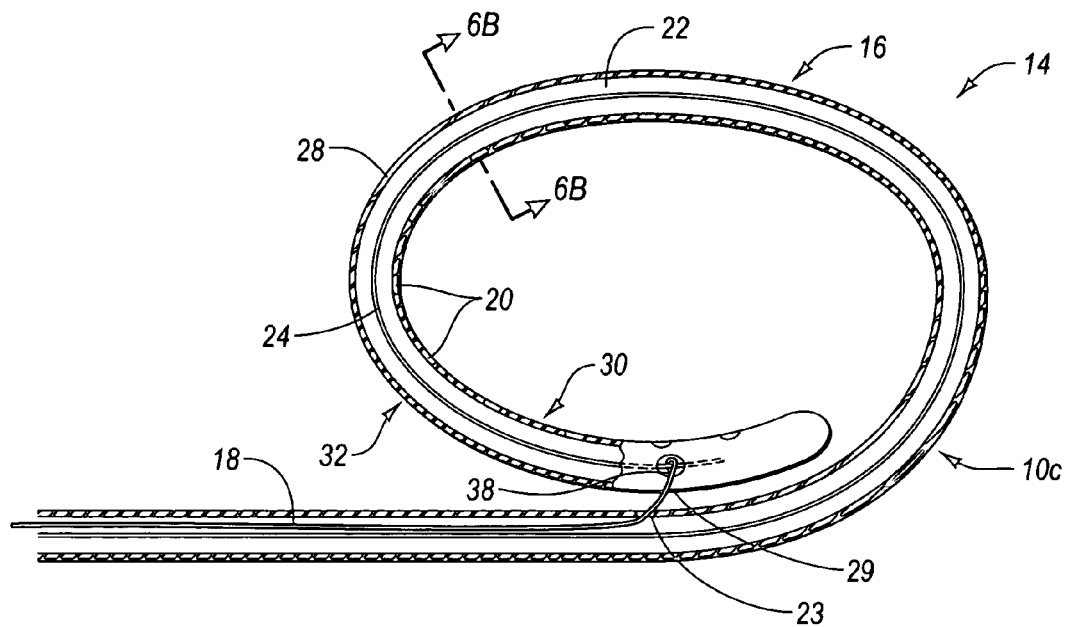
FIG. 6A is a cross-sectional end view of a drainage catheter having a stylet and stylet lumen positioned in a sidewall of the catheter.
Figure 6B:
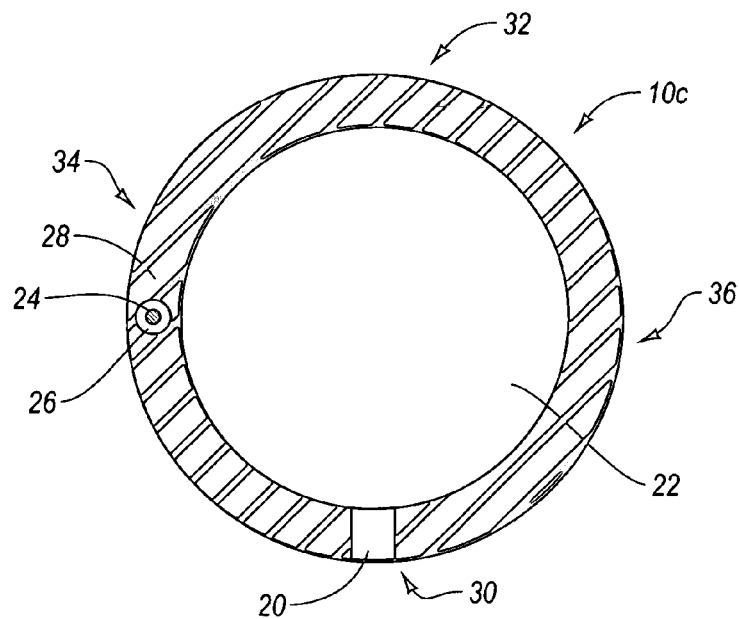
FIG. 6B is a cross-sectional side view of a drainage catheter having a stylet and stylet lumen positioned in the sidewall of the catheter.

FIGS. 6A and 6B illustrate a catheter tube 10c having a stylet 24 positioned in the sidewall of catheter 10c according to one embodiment of the present invention. In the illustrated embodiment, catheter tube 10c includes drainage bores 20, a lumen 22, a stylet 24, a stylet lumen 26, and a catheter wall 28. Catheter tube 10c includes an inside diameter 30, an outside diameter 32, a first lateral surface 34, and a second lateral surface 36. As previously discussed, drainage bores 20 are positioned on inside diameter 30 of loop 16 such that when the distal end 14 of the catheter tube 10c is looped in an anchor configuration, drainage of fluid into lumen 22 is not interrupted. Outside diameter 32 is on the side of catheter wall 28 opposite inside diameter 30 of loop 16. First lateral surface 34 and second lateral surface 36 are positioned on the opposite sidewalls of catheter wall 28 between inside diameter 30 and outside diameter 32 of loop 16.

In the illustrated embodiment, stylet 24 and stylet lumen 26 are positioned in first lateral surface 34 of catheter wall 28 approximately 90 degrees from the inside diameter 30. By being positioned in first lateral surface 34 of catheter wall 28, stylet 24 can extend through the portion of catheter tube 10c coterminous with drainage bores 20. Additionally, drainage bores 20 can be positioned on the inside diameter 30 of catheter tube 10c without obstruction from stylet 24. The positioning of stylet 24 renders it unnecessary for suture 18 to be threaded through the portion of lumen 22 corresponding with distal end 14. This permits the use of suture 18 in combination with stylet 24 without interfering with drainage bores 20 on the inside diameter of loop 16. Stylet 24 is shown in FIG. 6B utilizing phantom lines to depict the pathway of stylet 24 along the length of catheter tube 10c.

In the illustrated embodiment, suture 18 extends from lumen 22 through suture bore 23. Suture 18 then enters bore 29 such that the loop in the distal end of suture 18 wraps around sytlet 24. Loop 16 in the distal end of suture 18 is secured utilizing weld 38. Weld 38 provides a reliable and unobtrusive design for securing suture 18 to stylet 24. Because stylet 24 extends adjacent tip 44 of catheter tube 10c in first wall 34, neither stylet 24 nor suture 18 interfere with passage of fluid into drainage bores 20. As a result, suture 18 can be utilized in combination with stylet 24 to selectively secure and release loop 16 to anchor and allow removal of distal end 14 of catheter tube 10c.

During operation, stylet 24 secures suture 18 to tip 44 of catheter tube 10c in a simple and reliable manner. Suture 18 is utilized to secure tip 44 adjacent suture bore 23 to form loop 16 in order to anchor the drainage position of distal end 14 of catheter tube 10c. When the practitioner is ready to remove drainage catheter tube 10c from the patient, the user simply pulls stylet 24 in rearward direction. When the tip of stylet 24 passes bore 29, stylet 24 no longer secures suture 18. As a result suture 18 is released and the tip 44 of catheter tube 10c is no longer secured relative to suture bore 23. This releases the anchor provided by loop 16 and allows the practitioner to remove distal end 14 of catheter tube 10c in a simple and efficient manner.

In one embodiment of the present invention, the tip of stylet 24 extends past bore 29 a predetermined amount of distance in the distal direction. The actual distance that stylet 24 extends past bore 29 is configured such that when excessive strain is placed on catheter tube 10c, stylet 24 automatically releases suture 18. When excessive strain is placed on catheter tube 10c, the resilient nature of catheter tube 10c and/or the loop configuration of distal end 14 results in a small amount of stretching of catheter tube 10c. Although catheter tube 10c is stretched when forces are exerted on catheter tube 10c, stylet 24 is not stretched. As a result, stylet lumen 26 and bore 29 are stretched in a distal direction relative to stylet 24. When the forces exerted on catheter tube 10c exceed a predetermined amount of strain, bore 29 moves in a distal direction past the tip of stylet 24. As bore 29 moves past the tip of stylet 24, stylet 24 no longer secures suture 18 releasing suture 18 and allowing straightening of distal end 14 of catheter 10c. This allows the anchor configuration of loop 16 to be automatically released such that distal end 14 of catheter tube 10c can be removed from the patient. The ability to automatically release loop 16 provides additional safety and security in the event a practitioner attempts to withdraw distal end 14 of catheter tube 10c from the patient without first releasing suture 18 and/or stylet 24. Automatic realeasing of loop 16 can also be important in the event that the patient accidentally catches the catheter on an external surface or projection in the course of daily activities.

Figure 7:
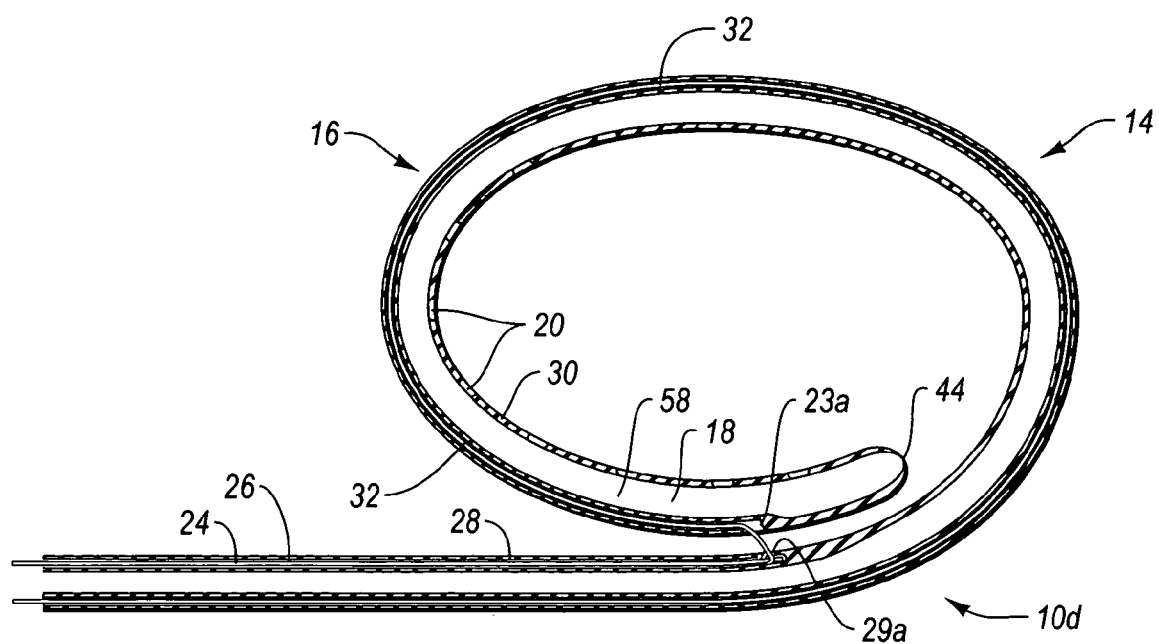
FIG. 7 is a cross-sectional side view of a drainage catheter having a stylet lumen and a suture lumen.

FIG. 7 is a cross-sectional side view of catheter tube 10d according to one embodiment of the present invention. In the illustrated embodiment, catheter tube 10d includes a suture lumen 58 and a stylet lumen 26 in the sidewall of catheter tube 10d. Stylet 24 and stylet lumen 26 extend to bore 29a in catheter tube 10d. Bore 29a is positioned proximally to distal end 14 at the point where tip 44 of catheter tube 10d is drawn to form loop 16. Suture lumen 58 is positioned in the sidewall of catheter 10d. In one embodiment, the suture lumen is positioned in one of the first lateral surface and the second lateral surface of the catheter wall. Suture lumen 58 extends from the proximal end of catheter 10d to approximately tip 44 of catheter tube 10d. Because suture lumen 58 is positioned in the sidewall of catheter 10d, suture 18 (depicted in phantom lines) can extend to the tip 44 of catheter tube 10d without being threaded through any portion of the lumen. This allows drainage of fluid through drainage bores 20 and along the length of the lumen without obstruction from suture 18.

The combination of suture lumen 58 and stylet lumen 26 allows suture 18 to extend to tip 44 of catheter 10d without interrupting the flow of fluids through drainage bores 20. In the illustrated embodiment, suture 18 is positioned in suture lumen 58 and extends from the proximal end of catheter 10d to the tip 44 of catheter 10d. Suture 18 exits the sidewall of catheter 10d at suture bore 23a. Suture 18 extends from suture bore 23a, enters bore 29a, and the loop in the distal end of suture 18 is wrapped around the distal end of stylet 24. To secure tip 44 adjacent bore 29a as depicted, the user exerts tension on suture 18. To temporarily release and/or reposition distal end 14, the user releases the tension on suture 18. To release distal end 14 and/or withdraw catheter tube 10d from the patient, the practitioner retracts the tip of stylet 24 past bore 29a. Once stylet 24 moves proximally past bore 29a, suture 18 is released.

As will be appreciated by those skilled in the art, a variety of types and configurations of catheter tubes can be utilized without departing from the scope and spirit of the present invention. For example, in one embodiment a suture lumen is utilized without the use of a stylet or stylet lumen. In another embodiment, a suture lumen extends to a proximal position on the catheter tube while a stylet and stylet lumen extend to the tip of the catheter tube. In another embodiment, both the suture lumen and the stylet lumen are positioned in the sidewall of the catheter tube. In yet another embodiment, one or both of the suture and the stylet lumen are positioned in the outside diameter of the catheter wall. In one embodiment, the cross-section of the drainage lumen is defined by the boundaries of the first and second sidewalls.

What is claimed is:

1. A drainage catheter for use in providing a fluid pathway for draining bodily fluid from a patient, the drainage catheter being configured to form a pig-tail-type loop at its distal end to secure the drainage position of the distal end of the catheter, the drainage catheter comprising:
    an elongate hollow tube having a proximal end and a distal end; a drainage lumen configured to allow passage of bodily fluids from the distal end of the elongate hollow tube to the proximal end of the elongate hollow tube;
    a hub positioned in fluid communication with the drainage lumen at the proximal end of the elongate hollow tube;
    an anchor loop adapted to be formed in the distal end of the elongate hollow tube such that the anchor loop has an inside diameter and an outside diameter, the anchor loop adapted to secure the drainage position of the distal end of the elongate hollow tube in a patient;
    a plurality of drainage bores positioned on the inside diameter of the anchor loop; and
    a stylet threaded along a length of the hollow tube, the stylet terminating at a position proximal to the drainage bores on the inside diameter of the anchor loop;
    a suture and a suture lumen positioned in one of the first and second sidewalls of the elongate hollow tube wherein the suture and suture lumen are positioned in the one of the first and second sidewalls of the hollow tube a determined amount of displacement from the inside diameter of the anchor loop such that the suture extends through the portion of the hollow tube coterminous with the drainage bores without the suture obstructing the passage of fluids into the drainage bores or the hollow tube or through the drainage lumen of the hollow tube and wherein the suture is threaded such that a single length of suture is positioned along the length of the hollow tube, the suture having a weld to secure one portion of the suture to another portion of the suture, the weld configured to selectively secure the suture to the stylet to selectively secure the configuration of the anchor loop.

2. The drainage catheter of claim 1, wherein the weld of the suture forms a loop in the suture.

3. The drainage catheter of claim 2, wherein the loop is positioned at a distal end of the suture.

4. The drainage catheter of claim 1, wherein the weld is formed utilizing ultrasonic energy applied to the portions of suture secured to one another.

5. The drainage catheter of claim 1, wherein the weld of the suture is utilized to secure the suture to the distal end of the elongate hollow tube.

6. The drainage catheter of claim 1, wherein the suture is secured directly to the distal end of the elongate hollow tube.

7. The drainage catheter of claim 1, wherein the suture is indirectly secured to the distal end of the elongate hollow tube.

8. The drainage catheter of claim 7, further comprising a stylet threaded in the elongate hollow tube.

9. The drainage catheter of claim 8, wherein the weld of the suture secures the suture to the stylet.

10. A drainage catheter for use in providing a fluid pathway for draining bodily fluid from a patient, the drainage catheter being configured to form a pig-tail-type loop at its distal end to secure the drainage position of the distal end of the catheter, the drainage catheter comprising:
    an elongate hollow tube having a proximal end, a distal end, a first sidewall, and a second side wall; a drainage lumen configured to allow passage of bodily fluids from the distal end of the elongate hollow tube to the proximal end of the elongate hollow tube, wherein the cross-section of the drainage lumen is defined by the boundaries of the first and second sidewalls of the tube;
    a hub positioned in fluid communication with the drainage lumen at the proximal end of the elongate hollow tube;
    an anchor loop formed in the distal end of the elongate hollow tube such that the anchor loop has an inside diameter and an outside diameter positioned between the first and second sidewalls of the elongate hollow tube, the anchor loop adapted to secure the drainage position of the distal end of the elongate hollow tube in a patient;
    a plurality of drainage bores positioned on the inside diameter of the elongate hollow tube;
    a stylet and stylet lumen positioned in one of the first and second sidewalls of the elongate hollow tube and extending along the length of the elongate hollow tube wherein the stylet and stylet lumen are positioned in one of the first and second sidewalls of the hollow tube a determined amount of displacement from the inside diameter of the hollow tube such that the stylet extends through the portion of the hollow tube coterminous with the drainage bores without the stylet obstructing the passage of fluids into the drainage bores of the catheter tube or through the lumen of the catheter tube; and
    a suture threaded along the elongate hollow tube and being secured to the stylet to selectively secure the configuration of the anchor loop.

11. The drainage catheter of claim 10, wherein the stylet is threaded through the stylet lumen.

12. The drainage catheter of claim 11, wherein the stylet and stylet lumen are positioned approximately 90 degrees from the inside diameter of the anchor loop.

13. The drainage catheter of claim 10, wherein one or more of the plurality of drainage bores are positioned on the inside diameter of the anchor loop.

14. The drainage catheter of claim 10, wherein the stylet and stylet lumen extend to the tip of the elongate hollow tube.

15. The drainage catheter of claim 14, wherein the suture exits the elongate hollow tube through a bore positioned proximally to the distal end of the elongate hollow tube.

16. The drainage catheter of claim 15, wherein the suture is secured to the stylet at the tip of the elongate hollow tube.

17. The drainage catheter of claim 16, wherein the suture draws the tip of the elongate hollow tube to the position of the bore positioned proximally to the distal end of the elongate hollow tube to form the anchor loop.

18. The drainage catheter of claim 17, wherein the user can release tension on the suture in order to release the configuration of the anchor loop.

19. The drainage catheter of claim 10, wherein the suture includes a weld to secure the configuration of the anchor loop.

20. The drainage catheter of claim 10, wherein the suture is welded to secure one portion of the suture to another portion of the suture to form a loon in the suture.

21. The drainage catheter of claim 20, wherein the loop is secured to the distal end of the stylet to selectively secure the anchor loop.

22. The drainage catheter of claim 21, wherein retraction of the stylet in a proximal direction releases the loop of the suture.

23. The drainage catheter of claim 22, wherein releasing the loop of the suture releases the anchor position of the distal end of the catheter.

24. The drainage catheter of claim 23, wherein the weld of the suture provides effective and unobtrusive securement of the loop.

25. A drainage catheter for use in providing a fluid pathway for draining bodily fluid from a patient, the drainage catheter being configured to form a pig-tail-type loop at its distal end to secure the drainage position of the distal end of the catheter, the drainage catheter comprising:

a catheter wall having a first side and a second side, the catheter wall defining the cross-section of the catheter;

a drainage lumen configured to allow passage of bodily fluids along the length of the catheter; a stylet and stylet lumen positioned in the catheter wall and threaded along the length of the catheter;

an anchor apparatus having an anchor configuration for selectively securing the drainage position of a distal end of the catheter; and a suture secured to the stylet to secure and release the anchor apparatus, wherein the suture is threaded through a bore adjacent a distal end of the stylet and is looped around the distal end of the sytlet, the distal end of the stylet extending in the stylet lumen only a predetermined distance in the distal direction past the bore such that when excessive force is exerted on the anchor apparatus, the resilient nature of the catheter wall and/or flexing of the stylet results movement one or the bore moves proximally relative to the distal end of the stylet permitting passage of the suture from around the distal end of the stylet and out of the bore automatically releasing the suture and the anchor configuration of the anchor apparatus.

26. The drainage catheter of claim 25, wherein the anchor apparatus comprises a loop formed in the distal end of the catheter.

27. The drainage catheter of claim 26, wherein the loop formed in the distal end of the catheter includes an inner diameter having a plurality of drainage bores positioned therein.

28. The drainage catheter of claim 27, wherein the stylet and stylet lumen are positioned in the catheter wall a determined amount of displacement from the inside diameter.

29. The drainage catheter of claim 28, wherein the stylet and stylet lumen are positioned approximately 90 degrees from the inside diameter.

30. The drainage catheter of claim 25, wherein the suture includes a weld to form a loop a distal end of the suture.

* * * * *